US005788863A

United States Patent [19]
Milunic

[11] Patent Number: 5,788,863
[45] Date of Patent: Aug. 4, 1998

[54] APPARATUS AND METHOD FOR CONDUCTING AN ASSAY USING REVERSE FLOW THROUGH A MEMBRANE

[75] Inventor: David Milunic, Cockeysville, Md.

[73] Assignee: Becton Dickinson and Company, Franklin Lakes, N.J.

[21] Appl. No.: 571,572

[22] Filed: Dec. 13, 1995

[51] Int. Cl.[6] .................................................. B01D 61/00
[52] U.S. Cl. ............................... 210/651; 210/656; 210/198.2; 210/321.75; 210/321.84; 210/416.1; 422/101
[58] Field of Search .......................... 210/651, 656, 210/198.2, 321.75, 321.84, 416.1, 321.72; 422/101

[56] References Cited

U.S. PATENT DOCUMENTS

| 4,806,313 | 2/1989 | Ebersole et al. | 422/100 |
|---|---|---|---|
| 4,897,193 | 1/1990 | Cais et al. | 210/450 |
| 4,960,130 | 10/1990 | Gurguis | 128/760 |
| 5,000,854 | 3/1991 | Yang | 210/321.72 |
| 5,022,411 | 6/1991 | Guirguis | 128/771 |
| 5,024,237 | 6/1991 | Guirguis | 128/760 |
| 5,079,170 | 1/1992 | Rosman et al. | 210/767 |
| 5,215,102 | 6/1993 | Guirguis | 128/771 |

Primary Examiner—Ana Fortuna
Attorney, Agent, or Firm—Susan A. Capello; Bruce S. Weintraub

[57] ABSTRACT

The present invention relates to an apparatus and method for conducting an assay using reverse flow through a membrane. More particularly, the present invention is directed to an apparatus and method which allows for the assaying of analytes, such as antigens, in a fluid sample containing such analytes with more accurate and reproducible results.

19 Claims, 5 Drawing Sheets

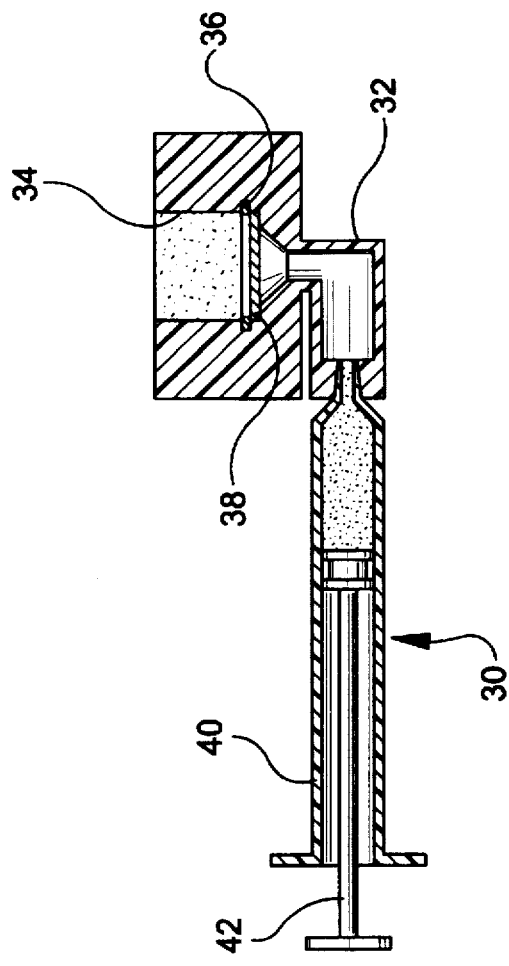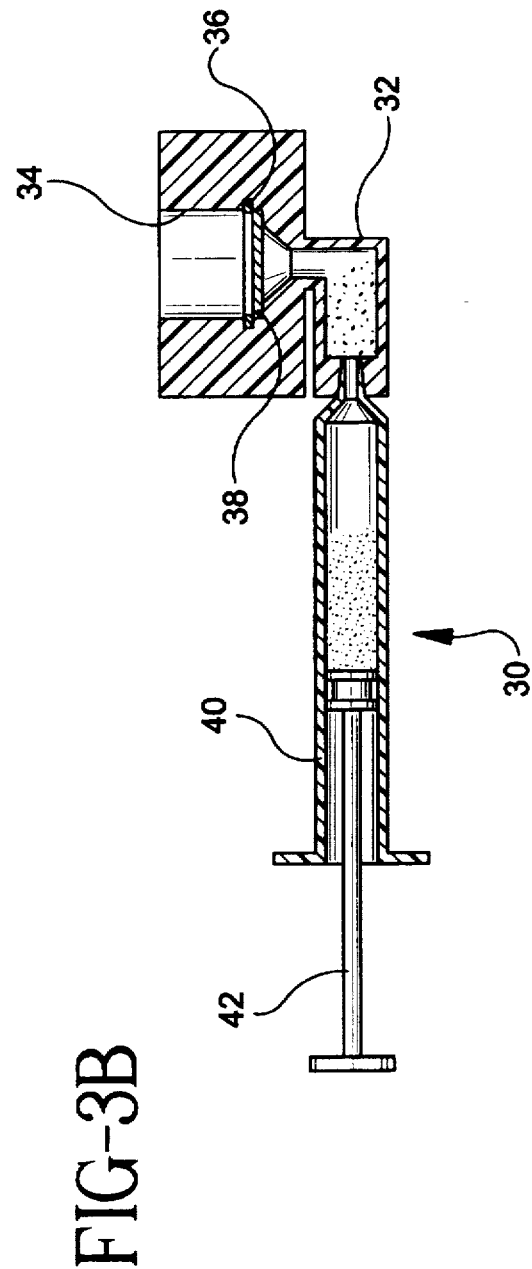

APPARATUS AND METHOD FOR CONDUCTING AN ASSAY USING REVERSE FLOW THROUGH A MEMBRANE

BACKGROUND OF THE INVENTION

1. Field of the Invention

The present invention relates to an apparatus and method for conducting an assay using reverse flow through a membrane. More particularly, the present invention is directed to an apparatus and method which allows for the assaying of analytes, such as antigens, in a fluid sample containing such analytes with more accurate and reproducible results.

2. Brief Description of Related Technology

Presently, when analytes are to be detected in fluid or liquid samples, the analyte-containing sample may be contacted with a membrane having the ability to retain the analyte. The membrane often has been pre-treated with a capture or binding agent—a material having the ability to interact with the analyte thereby enhancing the retention ability of the membrane. It is common in such systems for the membrane to be supported by glass wool or a fritted glass disk, and placed in a funnel-type apparatus. The funnel-type apparatus is capable of containing a certain volume of the sample, and through capillary action, gravimetric forces or the application of a vacuum on the funnel-type apparatus the analyte-containing sample is passed through the membrane. The purpose of this process is for at least a portion of the analyte from the sample to become retained on the membrane. The membrane may then be introduced to a detection means to determine the presence and/or quantity of the analyte so retained on the membrane. The amount or concentration of analyte in the sample may thus be calculated.

Certain problems, however, exist with such analyte retention systems. For instance, properties of the membranes, such as pore size, often vary from membrane-to-membrane even when manufactured to the purported same specifications. This is particularly so when the membranes are sourced from different lots or suppliers. Also when a binding agent is used with the membrane to form a capture phase, the amount or type of that agent may vary. In addition, when using such systems the time the sample is in contact with the membrane will ordinarily vary from sample-to-sample. This lack of uniformity from both the components and the use of the system translates into wide variations in the amount of analyte separated, which results in inaccuracies in the calculation of the quantity or concentration of the analyte in the sample. Clearly, when quantitative analyte detection is desired, this variability presents too great an uncertainty to consider such systems reliable.

It therefore would be desirable for an analyte retention system using membranes to normalize such inconsistencies and variations so as to allow sample assays to be more accurate, and more reproducible from sample-to-sample and from membrane-to-membrane.

SUMMARY OF THE INVENTION

The present invention solves the problems and desires referred to above by providing a device for separating an analyte from an analyte-containing fluid.

In one aspect of the invention, the device includes a body having a channel extending therethrough. The body includes a portion which is capable of receiving a fluid. The body also includes a fluid movement influencing portion which is coupled with a fluid moving means, such as a retractable plunger, to cause movement of the fluid through a membrane in both directions. Disposed between the fluid receiving portion and the fluid movement influencing portion is a membrane which is capable of retaining an analyte from an analyte-containing fluid contacted therewith. The device also includes the fluid moving means, such as the retractable plunger.

In another aspect of this invention, the device includes a reservoir having a fluid receiving portion and an analyte-retaining portion; a hollow cylinder, one end of which is adapted to join with the reservoir at the analyte-retention portion and another end of which is dimensioned to receive a fluid moving means, such as the retractable plunger; a membrane which is disposed between the analyte retention portion of the reservoir and the end of the hollow cylinder which is adapted to join the analyte retention portion of the reservoir; and a fluid moving means, such as the retractable plunger, which is dimensioned for retractable insertion within the hollow cylinder to cause movement of the fluid through the membrane in both directions.

In addition, a capture or binding agent and/or a detection component may be employed to facilitate the separation and/or detection of analytes of interest from analyte-containing fluids.

The present invention is also directed to a method for separating an analyte from an analyte-containing fluid and a kit for carry out such a method. The method includes the steps of contacting within a reservoir an analyte-containing fluid with a membrane; passing the fluid within the reservoir through the membrane and into a chamber; and detecting the analyte retained on the membrane.

As noted above, the present invention also contemplates a reverse flow membrane assay kit. The kit includes a device having a body with a fluid receiving portion and a means for moving fluid portion; a membrane; and a container in which is provided an amount of capture agent effective to form a capture phase with the membrane for interaction with an analyte contained in an analyte-containing fluid. Such interaction forms an analyte-capture phase complex. In addition, the kit may include a second container in which is provided an amount of detection component effective to interact with an analyte contained in the analyte-containing fluid. This interaction renders the analyte-detection component complex detectable.

The present invention is also directed to a method of using a fluid withdrawing/dispensing device in communication with a diffuser containing a membrane to separate an analyte from an analyte-containing fluid. This method includes the steps of contacting an analyte-containing fluid with a membrane; passing the fluid through the membrane; and detecting any analyte retained on the membrane.

With the devices and methods of the present invention, the passage of fluid through the membrane may be repeated to enhance separation quality and reproducibility from sample-to-sample.

The depictions in FIGS. 3A–3D represent a device according to the present invention in operation.

FIG. 3A depicts receipt of an analyte-containing fluid in the fluid receiving portion of a device according to the present invention.

FIG. 3B depicts withdrawal of the fluid moving means and passage of the analyte-containing fluid through the membrane of the device.

Figure 3C:
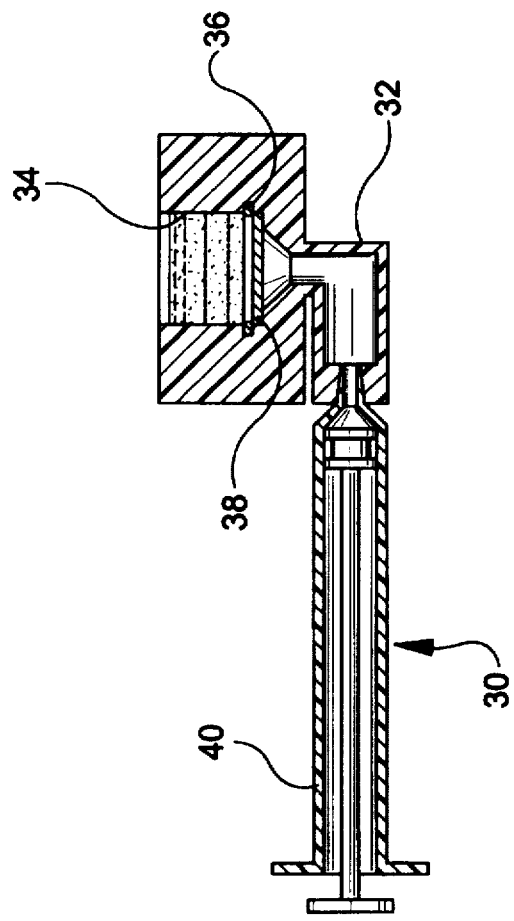

FIG. 3C depicts reinsertion of the fluid moving means and passage of the analyte-containing fluid back through the membrane of the device.

Figure 3D:
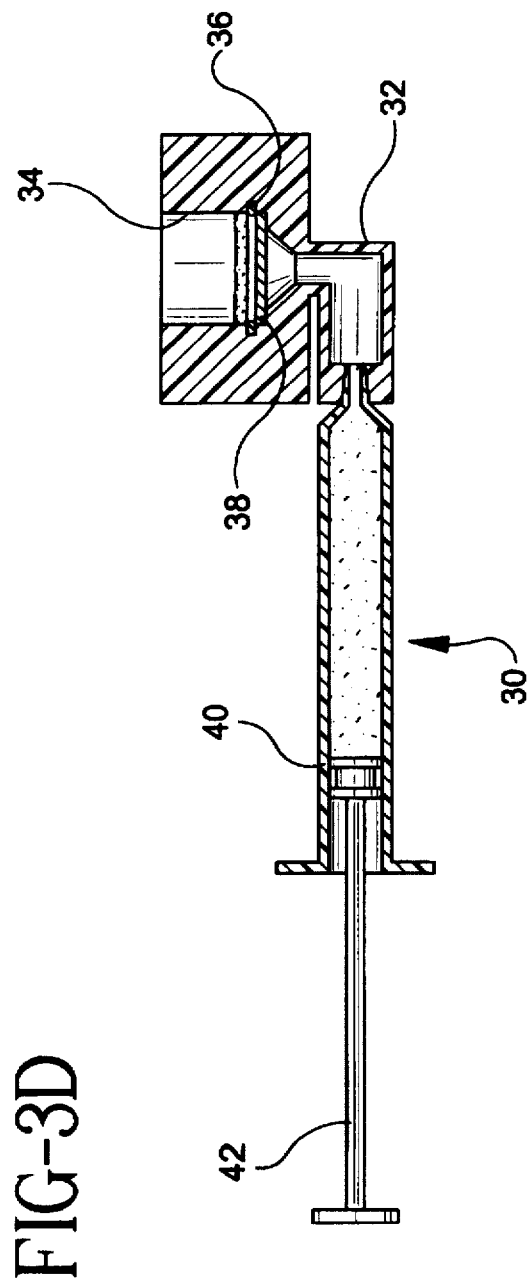

FIG. 3D depicts withdrawal of the fluid moving means and passage of fluid through the membrane of the device with analyte now retained on the membrane.

Figure 4B:
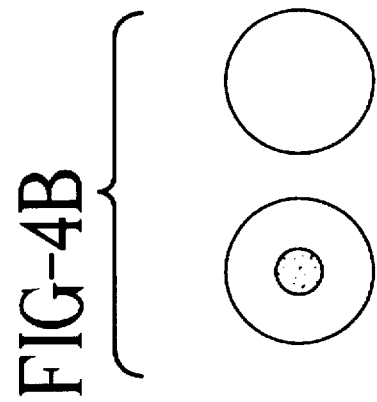
Figure 4A:
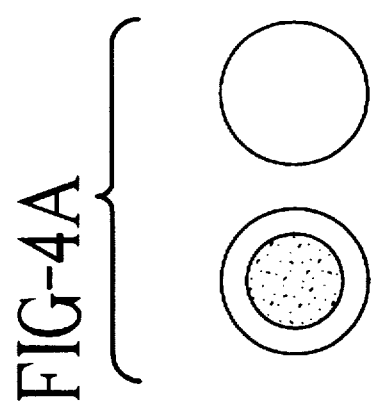

FIG. 4A depicts a comparison of two membranes, from a device in accordance with the present invention, the first of which having been contacted with an analyte-containing sample and the second of which having been contacted with a blank.

FIG. 4B depicts a comparison of two membranes, from a device in accordance with the present invention, the first of which having been contacted with an analyte-containing sample and the second of which having been contacted with a blank.

DETAILED DESCRIPTION OF THE INVENTION

The present invention is directed to a device for separating an analyte from an analyte-containing fluid. Broadly speaking, the device includes a body having a channel extending therethrough. The region of the channel in a first portion of the body is capable of receiving a fluid. In the region of the channel of a second portion of the body, the movement of fluid is influenced within the body by a fluid moving means, such as a retractable plunger. The fluid moving means, such as the retractable plunger, is coupled with the fluid movement influencing portion of the body to cause movement of the fluid through the membrane in both directions. Disposed between the fluid receiving portion and the fluid movement influencing portion is a membrane which is capable of retaining an analyte from an analyte-containing fluid contacted therewith. The region of the channel in the fluid receiving portion may be of a greater diameter than the region of the channel in the fluid movement influencing portion. The enhanced diameter of the region of the channel in the fluid receiving portion provides a landing on which the membrane may rest.

As noted above, the device may include a one-piece body. The device may also comprise a plurality of separate, but connectable components. In this situation, the device includes a hollow cylinder, such as a syringe barrel, and a reservoir, such as a diffuser. It may also be desirable to provide an "L"-shaped connection for placement between the hollow cylinder and the reservoir.

Figure 1:
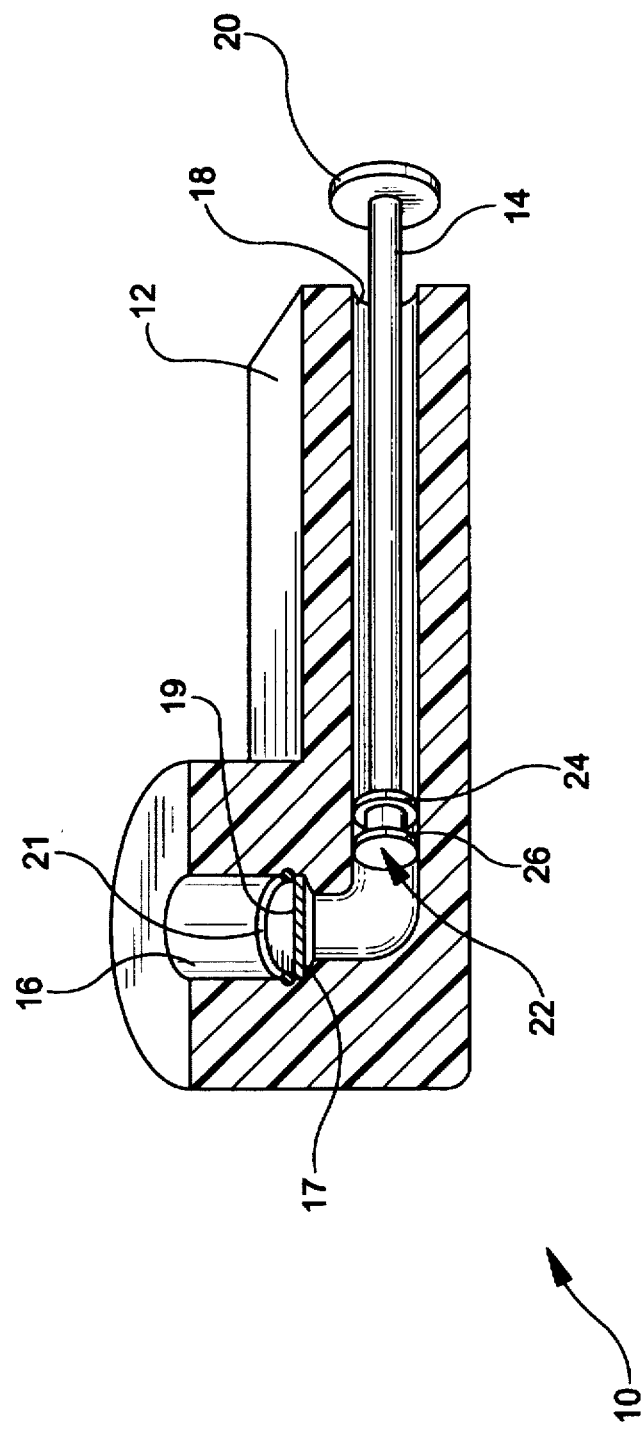
FIG. 1 is a side view of one embodiment of a device of the present invention, shown in partial cross-section.

With reference to the figures, FIG. 1 shows a device 10 according to the present invention. This device 10 includes a one-piece body 12 and a retractable plunger 14. The one-piece body may be constructed from a variety of materials, including acrylics, glass, metals, thermoset materials, thermoplastic materials, or any other material suitable to transfer fluids. As shown for example in FIG. 1, the one-piece body 12 of the device is in an "L" configuration. A straight configuration of this embodiment of the device is also within the scope of this invention. The device itself may be fabricated as a disposable item whose useful life is intended to be limited or it may be fabricated with the intention of allowing for reuse.

The one-piece body 12 includes a channel extending therethrough. At one end of the channel is a fluid receiving portion such as a reservoir 16, which is capable of receiving and containing a fluid disposed therein. At the other end of the channel is a fluid movement influencing portion 18, which is capable of receiving a means for influencing movement within the body, such as the retractable plunger 14. The reservoir 16 may be any shape as long as its interior is capable of receiving and containing a fluid sample. Similarly, it may be any size convenient to receive and contain the volume of sample of interest disposed therein.

The region of the channel extending through the one-piece body 12 which is within reservoir 16 has a diameter—inside diameter—which is greater than that of the region of channel extending through the remaining length of the one-piece body 12—i.e., the fluid movement influencing portion 18. Where these two portions of the one-piece body meet is a landing 17, which has the diameter of the region of the channel within the fluid movement influencing portion 18. The landing 17 provides support for the placement of a membrane 19 (see FIG. 1) into the reservoir 16.

In order to hold the membrane 19 in place, a membrane securing means 21, such as an O-ring, is placed thereover within the reservoir 16. This is particularly important when the plunger 14 is inserted within the fluid movement influencing portion to perform a fluid cycling operation. The O-ring may be constructed from a variety of inert and compressible materials including, but not limited to high impact polystyrene.

The plunger 14 has two ends. A first end includes a handle 20, which should remain external to the one-piece body 12. A second end ("the plunging end" 22) is situated within the fluid movement influencing portion 18. The plunging end 22 includes a plunger gasket 24 and a plunger head 26. The plunger gasket 24 and the plunger head 26 should be constructed of a material which is inert to the samples and their components, and, when used, the capture agents and/or the detection components. The plunger gasket 24 should also be compressible so as to form a tight seal in the channel within the fluid movement influencing portion 18. Suitable materials include teflon, silicone and rubber.

Figure 2A:
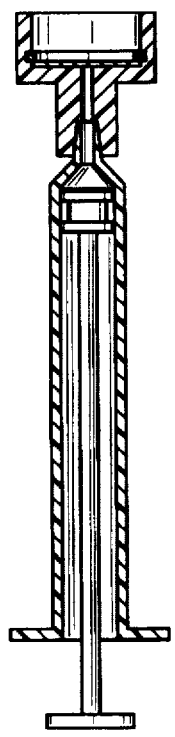
FIG. 2A is a side view of another embodiment of a device of the present invention, shown in partial cross-section.
Figure 2B:
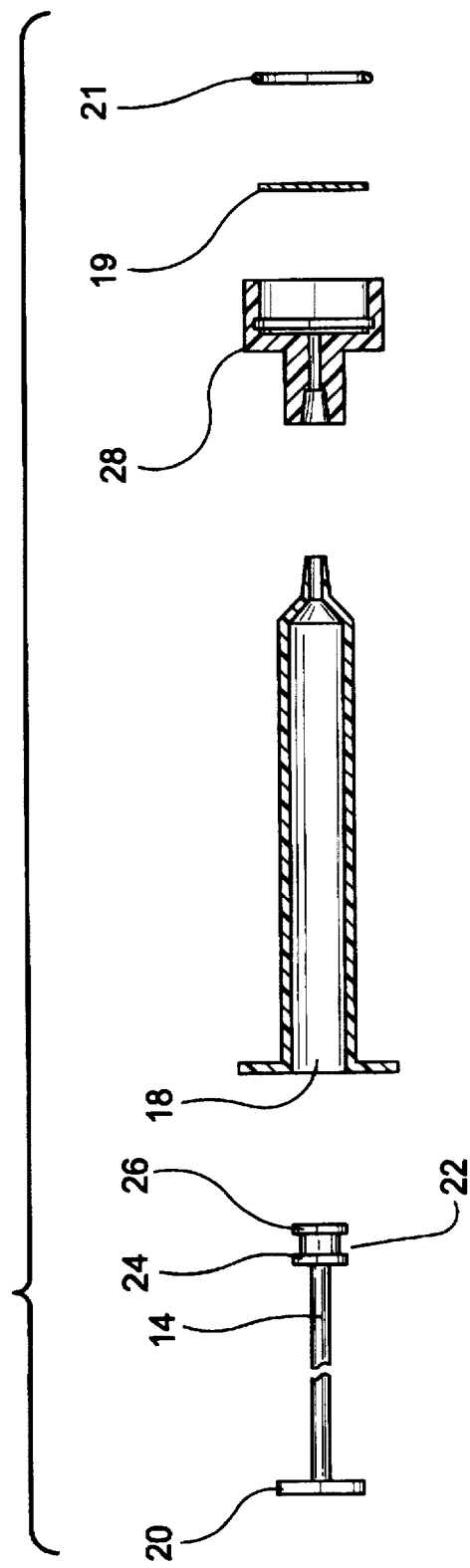
FIG. 2B is an exploded view of the embodiment shown in FIG. 2A.

In another aspect of the present invention as noted above and as seen in FIGS. 2A and 2B, the device may include a plurality of separate, but connectable components, such as a diffuser and cartridge 28. In addition, FIGS. 3A–3D show a device (in operation) in accordance with the present invention having an "L" configuration. More specifically, attached to a conventional tuberculin syringe 30 (such as one made by Becton Dickinson and Company, Franklin Lakes, N.J.) is one end of an "L"-shaped hollow connection 32. The other end of the "L"-shaped hollow connection is attached to a reservoir 34. A first end of the reservoir 34 is capable of receiving a fluid. The second end of the reservoir is attached to the "L"-shaped hollow connection 32 between its two ends. The internal diameter of the reservoir 34 narrows, and a membrane may be placed at that position where the diameter begins to narrow (see FIGS. 3A–3D). As with the device shown in FIG. 1, an O-ring 36 may be placed over the membrane 38 to secure it in place.

The connections may be made by conventional connection means, such as threaded connections, swage-lok connections, luer lock connections or any other convenient fluid-tight connection known to those of skill in the art.

The membrane used in the present invention may be selected from a variety of sources, such as nitrocelluloses, nylons, and polyesters. Preferred among these membranes are those made from nitrocellulose. A commercial source of nitrocellulose membranes suitable for use in connection with the present invention is Schleiser & Schuel, Keene, N.H., particularly catalog number AE100. Millipore Corporation, Bedford Mass., Pall Corporation, Port Washington, N.Y., and Whatman Inc., Fairfield, N.J..

Included on all or a portion of the membrane is a binding or capture agent which forms a capture phase. A capture phase may be included on one or both of the top/front and the rear/bottom surfaces of the membrane. The capture phase may include any of a variety of materials capable of interacting with an analyte of interest in a particular sample.

The type of interaction or incorporation will depend on the particular analyte in the fluid to be assayed and the capture or binding agent, if any, used to form the capture phase. By interaction is meant to include ionic bonding, covalent bonding, hydrogen bonding, bonding through van der Waals forces, bonding through electrostatic forces, incorporation through steric considerations, and magnetic considerations. Specific examples of types of interaction for the membrane and/or capture phase include size-exclusion or gel permeation interaction, antibody-antigen interaction, complementary nucleotide interaction, hormone-receptor interaction, ferromagnetic interaction, and hydrophobic interaction.

For instance, the capture phase may possess free basic or amino groups to interact with acidic groups in the sample, or the capture phase may possess free acidic groups to interact with basic or amino groups in the sample. Through this interaction, the analyte of interest should become incorporated with the capture phase and retained thereon so as to render the retained analyte available for detection.

In a preferred mode of the present invention, a capture agent is used to form a capture phase with the membrane, and the capture agent includes an antibody capable of interacting with and binding an antigen present in the sample to form a complex. For instance, an antibody which is appropriate for use in binding group A streptococcus antigen ("GAS Ag") is group A streptococcus antibody ("GAS IgG"). Other examples of complexes include thyroid stimulating hormone (TSH)/anti-TSH antibody complexes; human chorionic gonadotropin (hcG)/anti-hcG antibody complexes; sense strand DNA or RNA/anti-sense strand DNA or RNA, respectively, complexes; protein A/IgG complexes; streptavidin or avidin/biotin complexes; and noble metal/sulfhydryl group complexes.

Where the analyte to be detected does not itself possess physical characteristics rendering it readily detectable (e.g., having a chromophore detectable in the visible range of the electromagnetic spectrum), a detection component should be included. The detection component may be added to the sample to be assayed prior to introduction into the device. Alternatively, the detection component may be placed within the body of the device, such as within the fluid movement influencing portion 18, and mixed with the sample to be assayed as it is introduced to the reservoir 16 and passed through the membrane 19. In this way, the detection component may interact with the analyte of interest and form a complex therewith which is now capable of being detected. The analyte-detection component complex should interact with the capture phase in a manner like conventional sandwich assays.

The detection component may be selected from a variety of materials capable of interacting with an analyte of interest and capable of being detected. The detection component may be chosen from a host of fluorescent materials, UV-active materials, materials possessing a chromophore which is detectable in the visible range of the electromagnetic spectrum, radiolabel tags, and chemiluminescent materials. In addition, the detection component may be dormant (or not readily detectable by conventional detection means) prior to interacting with the analyte and there after becomes readily detectable using such detection means.

The detection means chosen to detect the membrane-retained analyte will depend on whether a detection component was employed in the assay and if one was so employed which particular one. Based on the teaching herein and on the state-of-the-art, those of skill in the art will be able to make appropriate choices of detection components and detection means.

FIGS. 3A–3D show a device according to the present invention in operation. In FIG. 3A, the device receives within the reservoir 34 an analyte-containing fluid. The analyte-containing fluid is then passed through a membrane 36 and into an "L"-shaped hollow connection 32. From the "L"-shaped hollow connection 32, the fluid continues to pass into a chamber, such as a hollow cylinder 40 (like the barrel of a syringe), by withdrawing therefrom the retractable plunger 42. (See FIG. 3B.)

The rate of fluid passage may be controlled so as to optimize sample contact time with the membrane 36. In order to enhance contact time with the membrane 36, the fluid may be recycled or passed through the membrane 36 in the opposite direction from which it came by applying force to the plunger 42 thereby reinserting it within the hollow cylinder 40. (See FIG. 3C.) By so doing, the fluid is driven back through the membrane 36 and into the reservoir 34. The fluid is then passed through the membrane 36 once again by withdrawing the retractable plunger 42 from within the hollow cylinder 40. (See FIG. 3D.)

This reversal of the direction of the flow of fluid may be performed a plurality of times so as to further enhance fluid-membrane contact time. With each pass of the fluid through the membrane, available analyte in the fluid interacts with the membrane to become incorporated therewith, provided the membrane has not been saturated. This reverse flow operation allows available analyte to separate from the fluid and concentrate on the membrane. The concentrated analyte retained on the membrane enhances a potentially otherwise low level of detectability.

As can be seen, this invention allows the user to control the flow rate of the fluid through the membrane with more precision than conventional methods of analyte detection using membranes. In the past, the rate of fluid flow in this regard was not scrutinized.

With the present invention, this greater control over the flow rate also benefits the reproducibility of observed from sample-to-sample.

The method of this invention may be lends itself to ready automation and random access methodology.

The present invention also contemplates a reverse flow membrane assay kit. The kit includes a device having a body with a fluid receiving portion and a means for moving fluid portion; a membrane; and a container in which is provided an amount of capture agent effective to form a capture phase with the membrane for interaction with an analyte contained in an analyte-containing fluid. Such interaction forms an analyte-capture phase complex. In addition, the kit may include a second container in which is provided an amount of detection component effective to interact with an analyte contained in the analyte-containing fluid. This interaction renders the analyte-detection component complex detectable.

The present invention is also directed to a method of using a fluid withdrawing/dispensing device in communication with a diffuser containing a membrane to separate an analyte from an analyte-containing fluid. The method includes the steps of contacting an analyte-containing fluid with a membrane; passing the fluid through the membrane; and detecting any analyte retained on the membrane.

In view of the above description of the present invention, it is clear that a wide range of practical opportunities is provided by the teaching herein. The following example of a device in accordance with the present invention and a method of its use, is provided for illustrative purposes only, and is not to be construed so as to limit in any the teaching herein.

EXAMPLE

A nitrocellulose membrane having a pore size of 12 μm [commercially available from Schleiser & Schuel under catalog number AE100 (lot number 1070/3)] was used in this example, together with a 1 cc tuberculin syringe (commercially available from Becton Dickinson and Company) and a two-piece cartridge and diffuser assembly (commercially available under catalog number 01-91(75) from Analtech, Newark, Del.). The membrane was placed flat within the cartridge and diffuser assembly, and secured in place with an O-ring. The O-ring, constructed from high impact polystyrene (white medium grade) and having a diameter of about 0.02", was made using a number 5 and number 3 cork borer and by cutting a small notch out of the side of the resulting O-ring.

As the analyte to be separated and detected from the sample in this example, an antigen, GAS Ag, was used at a concentration of $1 \times 10^9$ cells/ml, then diluted to 1:2000. As a detection component, GAS blue latex was used, which was prepared from 0.4 μm blue latex carboxyl modified [Bangs Labs], coupled to rabbit polyclonal antibody. A wash buffer, including phosphate buffer saline [whose components include sodium chloride (8 grams), potassium phosphate (0.2 grams), sodium phosphate (2.9 grams) and potassium chloride (0.2 grams) diluted to 1 liter with distilled water and adjusted to a pH of 7.5 with 1N sodium hydroxide] and 0.05% TWEEN, was used to dilute the detection component—the dilution used was 1 part GAS blue latex to 20 parts of the wash buffer. About 100 μl of this diluted detection component was preloaded into the barrel of the syringe. The membrane-containing cartridge and diffuser was thereafter mounted on the syringe.

As a capture agent in this example, an antibody, GAS IgG, was used at a concentration of about 1 mg/ml. About 1 μl of the GAS IgG was placed on the top/front face of the membrane, and thereafter 100 μl of the analyte-containing sample was introduced to the cartridge and diffuser assembly.

In a first run, the plunger of the syringe was withdrawn thereby causing the analyte-containing sample to pass through the membrane and into the syringe barrel. The plunger was then reinserted into the syringe barrel thereby forcing the sample to pass back through the membrane and into the assembly. During the withdrawal-reinsertion operation, the analyte-containing sample mixed with the diluted detection component within the barrel of the syringe. The rate at which this withdrawal-reinsertion operation was conducted was sufficient to establish 5 or 6 cycles per minute (one cycle constituting the sample fully withdrawn through the membrane and into the syringe barrel and then fully passed back through the membrane). This run was conducted over a period of time of about five minutes.

When compared to a blank in which no analyte had been placed, much background noise was observed in this first run of the sample. (See FIG. 4A.)

In a second run, in which all of the components of the analyte-containing sample and the detection component remained the same from the first run, the plunger of the syringe was withdrawn and reinserted at a rate sufficient to establish 2 cycles per minute. As with the first run, this run was conducted over a period of time of about five minutes.

In contrast to the first run of the sample, though, when the second run was compared to a blank in which no analyte had been placed, a tight blue spot was observed with little to no background noise. (See FIG. 4B.)

While the present invention has been described herein by way of illustration and example, it will be clear to those of skill in the art that changes and modifications many be made from the specific description without departing from the spirit and scope of the present invention defined by the claims.

What is claimed is:

1. A device for separating an analyte from an analyte-containing fluid, said device comprising a body having a channel extending therethrough, said body including:

a fluid receiving portion;

a fluid movement influencing portion;

a membrane disposed between said fluid receiving portion and said fluid influencing portion capable of retaining an analyte from an analyte-containing fluid contacted therewith;

fluid moving means coupled with said fluid movement influencing portion capable of moving the fluid through said membrane in two directions;

wherein said membrane includes a capture phase; and a detection component disposed in said device effective to interact with an analyte contained in the analyte-containing fluid forming an analyte detection component complex so as to render the analyte-detection component complex detectable.

2. The device according to claim 1, wherein said fluid moving means comprises a retractable plunger.

3. The device according to claim 1, wherein said analyte-containing fluid contains said detection component.

4. The device according to claim 3, wherein said detection component is group A streptococcus blue latex.

5. The device according to claim 1, wherein said membrane is constructed from nitrocellulose.

6. The device according to claim 1, wherein said analyte includes an antigen and said capture phase includes an antibody.

7. The device according to claim 6, wherein said antigen is group A streptococcus antigen and said antibody is group A streptococcus antibody.

8. The device according to claim 1 wherein the detection component is located in the fluid movement influencing portion.

9. The device according to claim 1 wherein the detection component is located in the channel.

10. The device according to claim 1 wherein the detection component is located in the fluid receiving portion.

11. The device according to claim 1 wherein the detection component is located in the fluid moving means.

12. A device for separating an analyte from an analyte-containing fluid, said device comprising:

a reservoir including at one end a fluid receiving portion capable of receiving a fluid and at the other end and analyte-retaining portion;

a hollow cylinder including at one end a portion adapted for joining said reservoir and said analyte-retaining portion and at the other end a portion dimensioned for receiving fluid moving means;

a membrane disposed between the analyte-retaining portion of said reservoir and the reservoir joining portion of said hollow cylinder;

fluid moving means dimensioned for retractable insertion within said hollow cylinder to cause movement of the fluid through said membrane in both directions; and a detection component disposed within the device effective to interact with an analyte contained in the analyte-containing fluid forming an analyte-detection component complex so as to render the analyte detection component complex detectable.

13. A method for separating an analyte from an analyte-containing fluid, said method comprising the steps of:

(a) mixing within a reservoir an analyte containing fluid an a detection component effective to interact with an analyte contained in the analyte-containing fluid forming an analyte-detection component complex, so as to render the analyte-detection component complex detectable;

(b) contacting the analyte-detection component complex with a membrane disposed in said reservoir;

(c) passing the fluid in the reservoir though the membrane and into a chamber;

(d) passing the fluid back from the chamber through the membrane and into the reservoir, and thereafter through the membrane into the chamber;

(e) detecting any analyte-detection component complex retained on the membrane.

14. A reverse flow membrane assay kit comprising:

a device including a body having a fluid receiving portion and a fluid movement influencing portion;

a membrane disposed in said body having a first and second faces; wherein said fluid movement influencing portion is capable of moving the fluid through said membrane in two directions with respect to said membrane faces;

a container in which is provided an amount of capture agent effective to form a capture phase with the membrane and interact with an analyte contained in an analyte-containing fluid so as to form an analyte-capture phase complex, and in which is provided an amount of detection component effective to interact with said analyte and said capture phase to form an analyte detection component complex, so as to render the analyte-detection component complex detectable.

15. A reverse flow membrane assay kit comprising:

a device including a body having a fluid receiving portion and a fluid movement influencing portion;

a membrane disposed within said fluid receiving portion; wherein said fluid influencing portion is capable of moving the fluid in two directions with respect to the membrane;

a container in which is provided an amount of capture phase agent effective to form a capture phase with the membrane and interact with an analyte contained in an analyte-containing fluid so as to form an analyte-capture phase complex; and a second container in which is provided an amount of detection component effective to interact with said analyte and said capture phase so as to form an analyte-detection component complex to render the analyte-detection component complex detectable.

16. A method of using a fluid withdrawing/dispensing device in communication with a diffuser containing a membrane to separate and analyte from an analyte-containing sample, said method comprising the steps of:

(a) introducing an analyte-containing fluid and a detection component in an amount of detection component effective to interact with an analyte contained in the analyte-containing fluid so as to form an analyte-detection component complex so as to render the analyte detection component complex detectable, into said fluid withdrawing/dispensing device;

(b) contacting the fluid with a membrane disposed in said device, and passing the fluid therethrough;

(c) passing the fluid back through the membrane in reverse direction; and (d) detecting any analyte-detection component complex retained on the membrane.

17. The method according to claim 16, wherein said analyte includes an antigen and said capture phase includes an antibody.

18. The method according to claim 17, wherein said antigen is group A streptococcus antigen and said antibody is group A streptococcus antibody.

19. The method according to claim 18, wherein said detection component is group A streptococcus blue latex.

* * * * *

UNITED STATES PATENT AND TRADEMARK OFFICE
CERTIFICATE OF CORRECTION

PATENT NO. : 5,788,863
DATED : Aug. 4, 1998
INVENTOR(S) : David Milunic

It is certified that error appears in the above-identified patent and that said Letters Patent is hereby corrected as shown below:

Claim 12, Line 4, after "end", delete "and" and substitute therefor --an--.
Claim 13, Line 4, delete "an" and substitute therefor --and--.
Claim 14, Line 4, delete "a".
Claim 14, line 5, delete ";" and substitute therefor --,--.
Claim 15, Line 4, delete ";" and substitute therefor --,--.
Claim 16, Line 3, delete "and" and substitute therefor --an--.

Signed and Sealed this

First Day of December, 1998

Attest:

BRUCE LEHMAN

*Attesting Officer*  *Commissioner of Patents and Trademarks*